US012767711B2

(12) United States Patent
Zheng et al.

(10) Patent No.: US 12,767,711 B2
(45) Date of Patent: Oct. 20, 2026

(54) ANTI-HUMAN NERVE GROWTH FACTOR ANTIBODY

(71) Applicant: Trinomab (Ningbo) Biotech Co., Limited, Ningbo (CN)

(72) Inventors: Weihong Zheng, Zhuhai (CN); Xiaoli Wang, Zhuhai (CN); Huizhen Gong, Zhuhai (CN); Junlang Liang, Zhuhai (CN)

(73) Assignee: TRINOMAB (NINGBO) BIOTECH CO., LIMITED, Ningbo (CN)

( * ) Notice: Subject to any disclaimer, the term of this patent is extended or adjusted under 35 U.S.C. 154(b) by 946 days.

(21) Appl. No.: 17/919,232

(22) PCT Filed: Apr. 13, 2021

(86) PCT No.: PCT/CN2021/087014

§ 371 (c)(1),
(2) Date: Oct. 14, 2022

(87) PCT Pub. No.: WO2021/208927

PCT Pub. Date: Oct. 21, 2021

(65) Prior Publication Data

US 2023/0151085 A1 May 18, 2023

(30) Foreign Application Priority Data

Apr. 17, 2020 (CN) ......................... 202010305924.8

(51) Int. Cl.
*C07K 16/22* (2006.01)
*A61K 39/395* (2006.01)
*A61P 29/00* (2006.01)
*C07K 14/48* (2006.01)
*C12N 15/63* (2006.01)
*G01N 33/68* (2006.01)

(52) U.S. Cl.
CPC .......... *C07K 16/22* (2013.01); *A61K 39/3955* (2013.01); *A61P 29/00* (2018.01); *C07K 14/48* (2013.01); *C12N 15/63* (2013.01); *G01N 33/6872* (2013.01); *C07K 2317/565* (2013.01); *C07K 2317/76* (2013.01); *C07K 2317/92* (2013.01); *G01N 2333/48* (2013.01)

(58) Field of Classification Search
None
See application file for complete search history.

(56) References Cited

U.S. PATENT DOCUMENTS 5,648,237 A 7/1997 Carter
5,789,199 A 8/1998 Joly et al.
5,840,523 A 11/1998 Simmons et al.
2012/0141484 A1 6/2012 Garcia-Martinez et al.
2019/0276548 A1 9/2019 Steiniger et al.

FOREIGN PATENT DOCUMENTS

AU 2012216653 B2 12/2013
CN 101107268 1/2008
CN 101827609 9/2010
CN 102358903 A 2/2012
CN 102408483 A 4/2012
CN 102746399 10/2012
CN 103619879 A 3/2014
CN 107760690 3/2018
CN 108623687 A 10/2018
CN 109929035 6/2019
CN 110467674 A 11/2019
CN 113527482 A 10/2021
EP 2 138 512 12/2009
EP 2364728 A1 9/2011
JP 2007537703 A 12/2007
JP 2008500274 A 1/2008
JP 2008527989 A 7/2008
JP 2010535509 A 11/2010
WO WO-2004/032852 4/2004
WO 2019177690 A1 9/2019
WO 2019201133 A1 10/2019

OTHER PUBLICATIONS

Angal et al., "A single amino acid substitution abolishes the heterogeneity of chimeric mouse/human (IgG4) antibody," Molecular Immunology (1993) 30(1):105-108.
"Anti-Nerve Growth Factor Monoclonal Antibody Tanezumab," Progress in Pharmaceutical Sciences (2010) 34(11):526-527 (machine translation included).
Carter, "Bispecific human IgG by design," Journal of Immunological Methods (2001) 248:7-15.
Chao et al., "Gene Transfer and Molecular Cloning of the Human NGF Receptor," Science (1986) 232(4749):518-521.
Chevalier et al., "Expression and functionality of the trkA proto-oncogene product/NGF receptor in undifferentiated hematopoietic cells," Blood (1994) 83(6):1479-1485.
Chothia et al., "Canonical structures for the hypervariable regions of immunoglobulins," J. Mol. Biol. (1987) 196:901-917.
Chothia et al., "Conformations of immunoglobulin hypervariable regions," Nature (1989) 342:877-883.
Dall'Acqua et al., "Properties of human IgG1s engineered for enhanced binding to the neonatal Fc receptor (FcRn)," The Journal of Biological Chemistry (2006) 281(33):23514-23524.
Flatman et al., "Process analytics for purification of monoclonal antibodies," Journal of Chromatography (2007) 848:79-87.
Garaci et al., "Anti-nerve growth factor Ab abrogates macrophage-mediated HIV-1 infection and depletion of CD4+ T lymphocytes in hu-SCID mice," PNAS (2003) 100(15):8927-8932.

(Continued)

*Primary Examiner* — Marianne P Allen
(74) *Attorney, Agent, or Firm* — Bayramoglu Law Offices LLC

(57) ABSTRACT

Provided are a neutralizing antibody, which can specifically bind to NGF, or an antigen-binding fragment thereof, and a preparation method for producing the antibody. Further provided is an application of the antibody in the treatment of NGF-related diseases or disorders, especially in relieving or improving individual pain.

8 Claims, 2 Drawing Sheets

Specification includes a Sequence Listing.

(56) References Cited

OTHER PUBLICATIONS

Gerngross, "Advances in the production of human therapeutic proteins in yeasts and filamentous fungi," Nature Biotechnology (2004) 22(11):1409-1414.
Graham et al., "Characteristics of a human cell line transformed by DNA from human adenovirus type 5," J. Gen. Virol. (1977) 36:59-72.
Hoyle, "Neurotrophins and lung disease," Cytokine & Growth Factor Reviews (2003) 14:551-558.
Idusogie et al., "Engineered antibodies with increased activity to recruit complement," The Journal of Immunology (2001) 166(4):2571-2575.
Kaneko et al., "Optimizing Therapeutic Anti-body Function: Progress with Fc Domain Engineering," Biodrugs (2011) 25(1):1-11.
Lazar et al., "Engineered antibody Fc variants with enhanced effector function," PNAS (2006) 103(11):4005-4010.
Li et al., "Optimization of humanized IgGs in glycoengineered Pichia pastoris," Nature Biotechnology (2006) 24(2):210-215.
Lommatzsch et al., "Neurotrophins in allergic airway dysfunction: what the mouse model is teaching US," Ann. N.Y. Acad. Sci (2003) 992:241-249.
Millan, "The induction of pain: an integrative review," Progress in Neurobiology (1999) 57:1-164.
Moore et al., "Engineered Fc variant antibodies with enhanced ability to recruit complement and mediate effector functions," mAbs (2010) 2(2):181-189.
Nakagawara, "Trk receptor tyrosine kinases: a bridge between cancer and neural development," Cancer Letters (2001) 169:107-114.
Natsume et al., "Engineered antibodies of IgG1/IgG3 mixed isotype with enhanced cytotoxic activities," Cancer Res. (2008) 68(10):3863-3872.
Reddy et al., "Elimination of Fc receptor-dependent effector functions of a modified lgG4 monoclonal antibody to human CD4," The Journal of Immunology (2000) 164:1925-1933.
Richards et al., "Targeting novel peripheral mediators for the treatment of chronic pain," British Journal of Anaesthesia (2013) 111(1):46-51.
Sarchielli et al., Nerve growth factor and chronic daily headache: a potential implication for therapy, Expert Review of Neurotherapeutics (2004) 4(1):115-127.
Shields et al., "High resolution mapping of the binding site on human IgG1 for Fc gamma RI, Fc gamma RII, Fc gamma RIll, and FcRn and design of IgG1 variants with improved binding to the Fc gamma R," The Journal of Biological Chemistry (2001) 276(9):6591-6604.
Stavenhagen et al., "Fc optimization of therapeutic antibodies enhances their ability to kill tumor cells in vitro and controls tumor expansion in vivo via low-affinity activating Fcgamma receptors," Cancer Res. (2007) 67(18):8882-8890.
Urlaub et al., "Isolation of Chinese hamster cell mutants deficient in dihydrofolate reductase activity," PNAS USA (1980) 77(7):4216-4220.
Wyman et al., "Promoter-activated expression of nerve growth factor for treatment of neurodegenerative diseases," Gene Therapy (1999) 6:1648-1660.
Yasuda et al., "Diabetic neuropathy and nerve regeneration," Progress in Neurobiology (2003) 69:229-285.
Zalevsky et al., "Enhanced antibody half-life improves in vivo activity," Nature Biotechnology (2010) 28(2):157-159.
Nancy E. Lane, et al., Tanezumab for the Treatment of Pain from Osteoarthritis of the Knee, New England Journal of Medicine, 2010, pp. 1521-1531, vol. 363, No. 16.

ANTI-HUMAN NERVE GROWTH FACTOR ANTIBODY

CROSS REFERENCE TO RELATED APPLICATIONS

This application is a national stage application under 35 U.S.C. § 371 of International Application No. PCT/CN2021/087014, filed internationally on Apr. 13, 2021, which claims priority to Chinese patent application No. 202010305924.8 filed Apr. 17, 2020. The contents of the above patent applications are incorporated by reference herein in their entireties for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 166102001200SEQLIST.TXT, date recorded: Oct. 14, 2022, size: 7,486 bytes).

TECHNICAL FIELD

The present application relates to the field of antibodies, in particular, to an antibody that specifically binds to NGF, a preparation method, and the use thereof.

BACKGROUND ART

Nerve growth factor (NGF) is the earliest discovered neurotrophin (neurotrophic factor), widely distributed in the brain, ganglia, iris, heart, spleen, placenta and other tissues, and fibroblasts, smooth muscle, skeletal muscle, glial cells, schwann cells, etc. NGF is a member of the neurotrophins (NT), a group of structurally related proteins that further include brain-derived neurotrophic factor (BDNF), NT-3, NT-4, NT-5 (Wyman et al. Gene Therapy (1999), 6: 1648-1660). The activity of NGF is mediated through two different membrane-bound receptors, the tyrosine kinase A (TrkA) receptor and the p75 receptor which is structurally related to other members of the tumor necrosis factor receptor family (Chao, et al. Science 232: 518-521, 1986).

NGF mediates a variety of diseases or conditions such as pain (RICHARDS, N. Br J Anaesth (2013), 111 (1): 46-51), arthritis, collagen vascular disease, demyelinating disease, airway inflammatory disease (Hoyle, Cytokine Growth Factor Rev (2003), 14:551-8; Lommatzsch, M. Ann NY Acad Sci (2003), 992:241-9), neurological disorder, metabolic disorders such as diabetes (Yasuda, H. Prog Neurobiol (2003), 69 (4): 229-85), diseases associated with viral infections (Garaci, E. PNAS (2003), 100 (15) 8927-8932), arrhythmias (W004/032852), psoriasis and cancer (Nakagawara, A. Cancer Lett (2001), 169(2): 107-14).

Peripheral tissue inflammation or nerve damage is the cause of pathophysiological pain. NGF can act to regulate the function of peripheral neurons and central neurons. It has been shown that NGF can interact with pain signaling systems in the body and cause hyperalgesia upon local or systemic administration to many species (Sarchielli, Expert Rev. Neurotherapeutics (2004), 4(1): 115-127).

Pain is a perception based on signals received from the surrounding environment and transmitted and interpreted by the nervous system (Millan, Prog. Neurobiol (1999). 57: 1-164). Severe pain affects the quality of life of human beings and places a huge economic burden on society. Therefore, the treatment of pain is one of the most common clinical and social demands. However, treatment of pain is only partially effective and many of these treatments themselves produce numerous adverse effects. Opioids, for example, have a good analgesic effect, but they are also nephrotoxins. At high doses, they tend to cause gastrointestinal irritation, ulceration, bleeding, and confusion. Even worse, long-term use of opioids is associated with drug tolerance and dependence.

Due to the enormous clinical need and market space in the area of pain, it is important and urgent to develop new drugs targeting pain pathways to treat pain. In recent years, with the increasing understanding of the role of NGF in acute and chronic pain and hyperalgesia, anti-NGF antagonists have become a new hotspot in the research of pain therapy. Many murine and humanized anti-NGF antibodies have been reported. Some anti-NGF antibody drug clinical trial data show positive results, however, the murine anti-NGF antibody and humanized anti-NGF antibody have problems of immunogenicity, etc.

Therefore, there is still a need in the art for compositions or methods that can be used to prevent or treat NGF-related diseases, such as compositions and methods that can be used to prevent or treat pain-related diseases or conditions. The present application can satisfy the need.

SUMMARY OF THE INVENTION

The present invention provides a novel antibody or antigen-binding fragment thereof capable of specifically binding to NGF with high affinity, particularly an antibody or antigen-binding fragment thereof that specifically binds to human NGF. In a preferred embodiment, the anti-NGF antibody provided herein is a human antibody that can cross-react with non-human NGF, including non-human primate NGF and/or mouse NGF. In another embodiment, the human antibody or antigen-binding fragment thereof described herein that specifically binds to human NGF is a neutralizing antibody that neutralizes NGF.

In one aspect, the present invention provides a human antibody or antigen-binding fragment thereof that specifically binds to human NGF and does not cross-react with neurotrophin-3 (NT-3), neurotrophin-4 (NT-4), brain-derived neurotrophic factor (BDNF). These antibodies are characterized by binding to NGF with high affinity and high specificity and are capable of neutralizing the activity of NGF.

In a particular embodiment, the anti-NGF antibody and antigenic fragment thereof comprises one, two, or three CDRs (preferably three CDRs) selected from the VH domain sequences of the antibodies shown in Table I. In another embodiment, the antibody of the present invention comprises one, two, or three CDRs (preferably three CDRs) selected from the VL domain sequences of the antibodies shown in Table I. In some embodiments, the antibody of the present invention comprises 6 CDR domain sequences of the antibodies shown in Table I. In a preferred embodiment, the CDR sequence of the antibody is the CDR sequence shown in Table II.

In some embodiments, the anti-NGF antibody or antigen-binding fragment thereof according to the present invention comprises A) a heavy chain CDR: (i) CDR1 comprising the amino acid sequence of SEQ ID NO: 1, or a sequence comprising acid substitutions (e.g. conservative substitutions), deletions or insertions of one or more and no more than 5 amino acids relative to the sequence, (ii) CDR2 comprising the amino acid sequence of SEQ ID NO: 2, or sequence comprising acid substitutions (e.g. conservative substitutions), deletions or insertions of one or more and no more than 3 amino acids relative to the sequence, (iii) CDR3 comprising the amino acid sequence of SEQ ID NO: 3, or sequence comprising acid substitutions (e.g. conservative substitutions), deletions or insertions of one or more and no more than 5 amino acids relative to the sequence, and B) a light chain CDR: (i) CDR1 comprising the amino acid sequence of SEQ ID NO: 4, or a sequence comprising acid substitutions (e.g. conservative substitutions), deletions or insertions of one or more and no more than 5 amino acids relative to the sequence, (ii) CDR2 comprising the amino acid sequence of SEQ ID NO: 5, or a sequence comprising acid substitutions (e.g. conservative substitutions), deletions or insertions of one or more and no more than 2 amino acids relative to the sequence, (iii) CDR3, comprising the amino acid sequence of SEQ ID NO: 6, or a sequence comprising acid substitutions (e.g. conservative substitutions), deletions or insertions of one or more and no more than 5 amino acids relative to the sequence, wherein an anti-NGF antibody comprising a modified CDR still has the ability to bind to NGF.

In some embodiments, the anti-NGF antibody or antigen-binding fragment thereof according to the present invention comprises A) a heavy chain CDR: (i) CDR1 consisting of the amino acid sequence of SEQ ID NO: 1, (ii) CDR2 consisting of the amino acid sequence of SEQ ID NO: 2, and (iii) CDR3 consisting of the amino acid sequence of SEQ ID NO: 3, and B) a light chain complementarity determining region (CDR): (i) CDR1 consisting of the amino acid sequence of SEQ ID NO: 4, (ii) CDR2 consisting of the amino acid sequence of SEQ ID NO: 5, and (iii) CDR3 consisting of the amino acid sequence set forth in SEQ ID NO: 6.

In some embodiments, the anti-NGF antibody or antigen-binding fragment thereof according to the present invention comprises a heavy chain variable region VH comprising or consisting of an amino acid sequence having an identity of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or more to the amino acid sequence of SEQ ID NO: 7. The anti-NGF antibody comprising the VH has the ability to bind to NGF. In some embodiments, the anti-NGF antibody or antigen-binding fragment thereof according to the present invention comprises a heavy chain variable region VH comprising the 3 heavy chain variable region CDRs of the antibodies shown in Table II and having an identity of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or more to the amino acid sequence of SEQ ID NO: 7. The anti-NGF antibody comprising the VH has the ability to bind to NGF. In some embodiments, the heavy chain variable region VH of the anti-NGF antibody comprises an amino acid sequence having one or more substitutions (e.g. conservative substitutions), insertions, or deletions relative to the amino acid sequence of SEQ ID NO: 7. The anti-NGF antibody comprising the VH has the ability to bind to NGF.

In some embodiments, the anti-NGF antibody or antigen-binding fragment thereof according to the present invention comprises a light chain variable region VL comprising or consisting of an amino acid sequence having an identity of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or more to an amino acid sequence of SEQ ID NO: 8. The anti-NGF antibody comprising the VL has the ability to bind to NGF. In some embodiments, the anti-NGF antibody or antigen-binding fragment thereof according to the present invention comprises a light chain variable region VL comprising the 3 light chain variable regions CDRs of the antibodies shown in Table II and having an identity of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or more to the amino acid sequence of SEQ ID NO: 8. The anti-NGF antibody comprising the VL has the ability to bind to NGF. In some embodiments, the light chain variable region VL of the anti-NGF antibody comprises an amino acid sequence having one or more substitutions (e.g. conservative substitutions), insertions, or deletions relative to the amino acid sequence of SEQ ID NO: 8. The anti-NGF antibody comprising the VH has the ability to bind to NGF.

In some embodiments, the anti-NGF antibody or antigen-binding fragment thereof according to the present invention comprises a heavy chain variable region (VH) and a light chain variable region (VL), wherein:

1) the heavy chain variable region VH comprises or consists of an amino acid sequence having an identity of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or more to the amino acid sequence of SEQ ID NO: 7; the light chain variable region VL comprises or consists of an amino acid sequence having an identity of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% or more to the amino acid sequence set forth in SEQ ID NO: 8, or
2) the heavy chain variable region VH comprises the heavy chain variable region CDR shown in Table II, and has an identity of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% to the amino acid sequence of SEQ ID NO: 7; the light chain variable region VL comprises the CDR of the light chain variable region shown in Table II and has an identity of at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% to the amino acid sequence of SEQ ID NO: 8; an anti-NGF antibody comprising the VH and VL has the ability to bind to NGF, or
3) the heavy chain variable region VH comprises an amino acid sequence having one or more substitutions (e.g. conservative substitutions), insertions, or deletions relative to the amino acid sequence of SEQ ID NO: 7; the light chain variable region VL comprises an amino acid sequence having one or more substitutions (e.g. conservative substitutions), insertions, or deletions relative to the amino acid sequence of SEQ ID NO: 8; the anti-NGF antibody comprising the VH and VL has the ability to bind to NGF.

In a preferred embodiment, the present invention provides an anti-NGF antibody or antigen-binding fragment thereof, wherein the heavy chain variable region VH comprises or consists of the amino acid sequence shown in SEQ ID NO: 7; the light chain variable region VL comprises or consists of the amino acid sequence set forth in SEQ ID NO: 8.

In some embodiments, the anti-NGF antibody or antigen-binding fragment thereof further comprises heavy and/or light chain constant region sequences from a human antibody germline consensus sequence. The light chain constant region is preferably a human kappa (CK) or lambda (Cλ) chain constant region. The heavy chain constant region can be a γ, μ, α, δ, or ε chain. In some embodiments, the heavy chain constant region is a human IgG1, IgG2, IgG3, IgG4, IgA1, IgA2, IgM, IgD, and IgE isotype. Each heavy, light chain type is characterized by specific constant regions having sequences well known in the art.

In some embodiments, the constant region is preferably a human IgG constant region, such as a human IgG1, IgG2, IgG3, or IgG4 isotype constant region. In some embodiments, the heavy and/or light chain constant regions are as described, for example, in Sequences of Proteins of Immunological Interest, NIH Publication No. 91-3242, any of which may be used in the present invention.

In a preferred embodiment, the present invention provides an anti-NGF antibody or antigen-binding fragment thereof, wherein the heavy chain constant region is a human IgG4 constant region, and the heavy chain constant region sequence comprises or consists of the amino acid sequence shown in SEQ ID NO: 9; the light chain variable region VL comprises or consists of the amino acid sequence set forth in SEQ ID NO: 10.

It will be appreciated that sequence variants of these constant region domains may also be used, for example comprising one or more amino acid modifications in which the amino acid positions are identified in accordance with the EU indexing system of Kabat, et al. (1991).

In some embodiments, a modification is made e.g. in the human IgG constant region to prevent glycosylation of the antibody, and the modification may be N297A or N297Q (Sazinsky, PNAS (2008), 105 (51): 20167-20172).

In some embodiments, a modification is made e.g. in the human IgG constant region to alter Fc receptor interactions, and the modification may be L234A and/or L235E or L235A.

In some embodiments, a modification is made e.g. in the human IgG constant region to increase the half-life, and the modification may be R435H.

In some embodiments, a modification is made e.g. in the human IgG constant region to prevent or reduce chain exchange, and the modification may be S228P (Angal, S. Mol Immunol (1993), 30: 105-108).

In some embodiments, a modification is made e.g. in the human IgG constant region to enhance FcRn binding, and the modification may be M252Y, S254T, T256E (DallAcqua et al. J. Biol. Chem (2006), 281 (33): 23514-23524; Zalevsky et al. Nature Biotech (2010), 28 (2): 157-159), M428L or N434S.

In some embodiments, a modification is made e.g. in the human IgG constant region to alter antibody-dependent cytotoxicity (ADCC), and/or complement-dependent cytotoxicity (CDC), for example, and the modification is known (including but not limited to: Natsume et al. Cancer Res (2008), 68 (10): 3863-72; Idusogie et al. J. Immunol (2001), 166 (4): 2571-5; Moore et al. mAbs (2010, 2 (2): 181-189; Lazar et al. PNAS (2006), 103 (11): 4005-4010; Shields et al. J. Biol. Chem. (2001), 276 (9): 6591-6604; Stavenhagen Cancer Res (2007), 67(18): 8882-8890; Alegre et al. J. Immunol (1992) 148: 3461-3468; Kaneko, Niwa et al. Biodrugs (2011), 25 (1): 1-11).

In some embodiments, heterodimerization can also be induced by T366W modification, and optionally further by the introduction of disulfide bonds via S354C and Y349C modifications on opposite CH3 domains (Carter, Journal of Immunological Methods (2001), 248:7-15).

In some embodiments, the antibodies of the present invention also encompass antibodies that compete with any of the antibodies described above for binding to NGF, as well as antibodies that bind to the same epitope of NGF as any of the antibodies described above.

In some embodiments, at least a portion of the framework sequence of the anti-NGF antibody is a human consensus framework sequence.

In an embodiment, the anti-NGF antibody of the present invention is an intact antibody such as IgG1, IgG2, IgG3, IgG4, IgM, IgA, and IgE antibodies. In another embodiment, the anti-NGF antibody of the present invention encompasses only antigen-binding portions thereof, e.g. Fab, Fab'-SH, Fv, scFv, or $(Fab')_2$ fragments. In an embodiment, the anti-NGF antibody of the present invention can be modified to achieve a certain function, e.g. to eliminate residual effector function (Glu can eliminate residual effector function (Reddy et al. 2000)).

In some embodiments, the anti-NGF antibody of the present invention is a neutralizing antibody for neutralizing NGF.

In a second aspect, the present invention provides a nucleic acid encoding any of the above anti-NGF antibodies or fragments thereof. In an embodiment, a vector comprising the nucleic acid is provided. In an embodiment, the vector is an expression vector.

In a third aspect, the present invention provides a host cell comprising the vector or comprising the nucleic acid or antibody. In an embodiment, the host cell is a eukaryotic cell. In another embodiment, the host cell is selected from a mammalian cell, such as a CHO cell, a HEK293 cell, a COS cell, or other cells suitable for the production of the antibody or antigen-binding fragment thereof. In another embodiment, the host cell is a prokaryotic cell, e.g., an *E. coli* cell, or a yeast cell.

In a fourth aspect, the present invention provides a method of preparing an anti-NGF antibody or antigen-binding fragment thereof, wherein the method comprises culturing the host cell under conditions suitable for expressing a nucleic acid encoding the antibody or antigen-binding fragment thereof and optionally isolating the antibody or antigen-binding fragment thereof. In a certain embodiment, the method further comprises recovering the anti-NGF antibody or antigen-binding fragment thereof from the host cell.

In some embodiments, the present invention provides anti-NGF antibodies or antigen-binding fragments thereof produced by the method of the present invention.

In a fifth aspect, the present invention provides a composition comprising any of the anti-NGF antibody or antigen-binding fragment thereof described herein; preferably, the composition is a pharmaceutical composition.

In an embodiment, the composition further comprises a pharmaceutical vector. In an embodiment, the anti-NGF antibody and antigen-binding fragment thereof comprised in the composition are conjugated to a conjugation moiety. In an embodiment, the pharmaceutical composition further comprises a pharmaceutically acceptable carrier, excipient, or diluent.

In a sixth aspect, the present invention provides a method for treating a disease or disorder associated with NGF, comprising administering a therapeutically effective amount of an anti-NGF antibody of the present invention, or administering a pharmaceutical composition of the present invention, to a subject.

The present invention also relates to a method for alleviating or ameliorating symptoms associated with NGF-mediated diseases or disorders, comprising administering a therapeutically effective amount of an anti-NGF antibody of the present invention, or administering a pharmaceutical composition of the present invention, to a subject.

In a particular embodiment, the NGF-mediated disease or condition encompasses any medical disease or condition associated with elevated NGF levels or increased sensitivity to NGF, including but not limited to pain, arthritis, collagen vascular disease, demyelinating disease, airway inflammatory disease, neurological disease, metabolic disease (such as diabetes), disease associated with viral infection, cardiac rhythm disorder, psoriasis, and cancer.

In an embodiment, the NGF-mediated disease or disorder is a pain-related disorder, inflammatory pain, post-surgical incision pain, neuropathic pain, fracture pain, gout joint pain, burning pain, cancer pain, complex regional pain syndrome, post-herpetic neuralgia, or pain associated with sickle cell crisis. In an embodiment, the pain is pathophysiological pain.

Further, the method can ameliorate, alleviate, inhibit or prevent any disease or condition associated with NGF, or alleviate symptoms associated with the disease, such as pain, by eliminating, inhibiting, or reducing the activity of NGF. In an embodiment, the present invention can treat the disease or condition associated with NGF by administering an anti-NGF antagonist, such as an antibody or antigen-binding fragment thereof, of the present invention alone. In another embodiment, according to the presently disclosed method of treatment, the anti-NGF antibody is administered in combination with a second therapeutic agent selected from other neurotropins, analgesics, anti-inflammatory agents, chemotherapeutant and immunotherapeutic agents for the treatment of a disease or condition associated with NGF agents. In a particular embodiment, the second therapeutic agent is another neurotrophin, such as NT-3, NT-4, or BDNF.

In an embodiment, the present invention provides a method of alleviating or ameliorating NGF-mediated pain comprising administering a therapeutically effective amount of an anti-NGF antibody of the present invention, or a therapeutically effective amount of a pharmaceutical composition, to a subject.

In a seventh aspect, the present invention provides a method of detecting NGF in a subject or sample, the method comprising: (a) contacting a subject or sample with any of the anti-NGF antibodies or fragments thereof described herein; and (b) detecting the formation of a complex between the anti-NGF antibody or fragment thereof and NGF. In a preferred embodiment, the anti-NGF antibody and antigen-binding fragments thereof according to the present invention further comprise a detectable label.

In an embodiment, the antibody provided herein can be used to detect, diagnose, and monitor diseases or disorders associated with altered or aberrant NGF expression.

In an eighth aspect, the present invention relates to the use of any of the anti-NGF antibody or fragment thereof described herein in the manufacture of a medicament or kit for treating a disease or condition associated with NGF in a subject.

In an embodiment, the present invention provides the use of a composition comprising the anti-NGF antibody in the manufacture of a medicament or a kit for treating a disease or condition associated with NGF in a subject.

In another embodiment, the present invention also relates to the use of any anti-NGF antibody or fragment thereof described herein, or a composition comprising the anti-NGF antibody, in the manufacture of a medicament for alleviating or ameliorating NGF-mediated pain.

In another embodiment, any anti-NGF antibody or fragment thereof herein is used as a medicament.

In a ninth aspect, the present invention provides a kit, e.g. a diagnostic kit, a detection kit, a therapeutic kit, etc. comprising an antibody or composition of the present invention.

The present invention also encompasses any combination of any of the embodiments described herein. Any of the embodiments described herein, or any combination thereof, is applied to any or all anti-NGF antibodies or fragments thereof, methods, and uses of the present invention described herein.

Beneficial effects of the present invention:

The present invention provides human antibody and antigen-binding fragments thereof capable of specifically recognizing/binding to NGF, the antibody and antigen-binding fragment thereof having neutralizing effect against NGF and not cross-reacting to NT-3, NT-4, and BDNF. Since the anti-NGF antibody of the present invention are fully human antibodies, they have low immunogenicity to a subject while treating a disease or condition associated with NGF, or relieving pain associated with NGF, thereby effectively avoiding a corresponding immune response against the subject, thereby reducing side effects associated with conventional anti-NGF antibodies.

DETAILED DESCRIPTION OF THE INVENTION

1.1 Definitions

Figure 1:
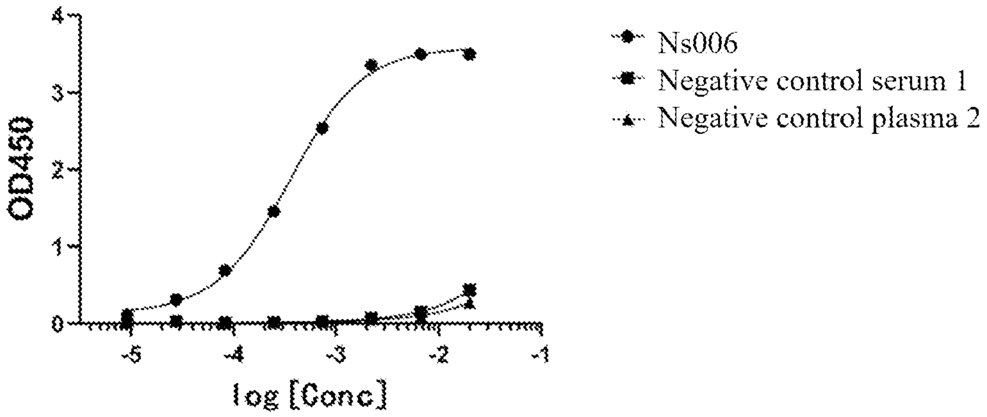
FIG. 1: test results of anti-NGF antibody titer of a sample (Ns006)

Before the present invention is described in detail below, it is to be understood that the present invention is not limited to the particular methodology, protocols, and reagents described herein, as these may vary. It is also to be understood that the terminology used herein is for the purpose of describing specific embodiments only and is not intended to limit the scope of the invention, which shall be limited only by the appended claims. Unless otherwise defined, all technical and scientific terms used herein have the same meaning as commonly understood by one of ordinary skill in the art to which this invention belongs.

For purposes of interpreting the description, the following definitions will be used and whenever appropriate, terms used in the singular may also include the plural and vice versa. It is to be understood that the terminology used herein is for the purpose of describing particular embodiments only and is not intended to be limiting.

The term "about" when used in conjunction with a numerical value is intended to encompass numerical values within a range having a lower limit that is 5% less than the numerical value specified, and an upper limit that is 5% greater than the numerical value specified.

The term "and/or" should be understood to mean either one of the alternatives or both of the alternatives.

As used herein, the terms "comprise" or "include" means including the recited elements, integers or steps but not excluding any other elements, integers or steps. As used herein, the terms "comprise" or "include" when used herein, unless otherwise indicated, encompass the case consisted by the stated elements, integers, or steps. For example, reference to an antibody variable region "comprising" a particular sequence is also intended to encompass antibody variable regions consisting of that particular sequence.

The term "nerve growth factor" or "NGF" refers to the native sequence NGF of all mammalian species, including humans, and encompasses any form thereof that retains at least part of the biological activity of NGF, such as NGF mutants, NGF orthologs, NGF paralogs, and the like.

The term "antibody" is used herein in the broadest sense and encompasses a variety of antibody structures, including, but not limited to, monoclonal antibodies, polyclonal antibodies, multispecific antibodies (e.g. bispecific antibodies), and antibody fragments, so long as they exhibit the desired antigen binding activity. An intact antibody will typically comprise at least two full-length heavy chains and two full-length light chains, but in some cases may comprise fewer chains, for example, an antibody naturally occurring in camels may comprise only heavy chains.

As used herein, a "monoclonal antibody" or "mAb" refers to an antibody derived from a single copy or clone of, for example, a eukaryotic, prokaryotic, or phage clone, i.e. the individual antibodies that make up the population are identical and/or bind the same epitope except for possible variant antibodies (e.g. those containing natural mutations or produced during the manufacture of monoclonal antibody preparations) which are typically present in minor amounts. The modifier "monoclonal" refers to the characteristic that an antibody is obtained from a substantially homogeneous population of antibodies, and should not be construed as requiring the production of the antibody by any particular method. Monoclonal antibodies may be produced, for example, by hybridoma techniques, recombinant techniques, phage display techniques, synthetic techniques such as CDR grafting, or combinations of these or other techniques known in the art.

A "native antibody" refers to a naturally occurring immunoglobulin molecule having a different structure. A "native sequence Fc domain" comprises an amino acid sequence that is identical to the amino acid sequence of an Fc domain found in nature. Native sequence human Fc domains include, for example, native sequence human IgG1 Fc domains (non-A and A allotypes); a native sequence human IgG2 Fc domain; a native sequence human IgG3 Fc domain; and a native sequence human IgG4 Fc domain; and naturally occurring variants thereof.

"Human antibody" refers to an antibody having an amino acid sequence that corresponds to the amino acid sequence of an antibody produced by a human or human cell or derived from a non-human source, which utilizes a human antibody repertoire or other human antibody coding sequence. This definition of human antibodies specifically excludes humanized antibodies comprising non-human antigen-binding residues.

The term "neutralizing antibody" is an antibody or antibody fragment that reduces or inhibits the biological activity of NGF, such as reducing or inhibiting the binding of NGF to one or more of its receptors, preferably TrkA. The reduction in biological activity may be a partial reduction or a complete reduction. The extent to which an antibody neutralizes NGF is referred to as the neutralizing potency of the antibody. The neutralizing potency of an antibody can be determined or measured using one or more assays known to those of ordinary skill and/or described or referred to herein, including, but not limited to, the competitive binding assay, direct and indirect sandwich assay, immunoprecipitation assay and enzyme-linked immunosorbent assay (ELISA).

"Anti-NGF antibody" refers to an antibody that binds to NGF and inhibits the biological activity of NGF and/or downstream pathways mediated by NGF signaling. Anti-NGF antibodies comprise antibodies that block, antagonize, inhibit or reduce (including significantly reduce) NGF biological activity, including downstream pathways mediated by NGF signaling such as receptor binding and/or eliciting a cellular response to NGF.

In some embodiments, the present invention also encompasses fragments of anti-NGF antibodies. Examples of antibody fragments include, but are not limited to, Fv, Fab, Fab', Fab'-SH, $F(ab')_2$, diabodies, linear antibodies, single-chain antibody molecules (e.g. scFv); and multispecific antibodies formed from antibody fragments.

"Biological activity" of an NGF generally refers to the ability to bind to the NGF receptor and/or activate the NGF receptor signaling pathway. For example, the biological activity includes any one or more of the following: the ability to bind to NGF receptors such as p75 and/or TrkA; the ability to promote TrkA receptor dimerization and/or TrkA autophosphorylation; the ability to activate NGF receptor signaling pathways; the ability to promote cell differentiation, proliferation, survival, growth and other changes in cell physiology; the ability to promote survival of mouse E13.5 trigeminal neurons and to mediate pain, including post-surgical pain.

Each heavy chain consists of a heavy chain variable region (HCVR or VH) and a heavy chain constant region. The heavy chain constant region consists of three domains, CH1, CH2, and CH3. Each light chain consists of a light chain variable region (LCVR or VL) and a light chain constant region. The light chain constant region consists of one domain, CL. The VH and VL regions can be further divided into hypervariable regions called complementary determining regions (CDR), interspersed with more conserved regions called framework regions (FR). Each VH and VL consists of three CDRs and four FRs, arranged from amino-terminus to carboxy-terminus in the following order: FR1, CDR1, FR2, CDR2, FR3, CDR3, FR4.

A "complementarity determining region" or "CDR region" or "CDR" or "hypervariable region" is a region of an antibody variable region that is primarily responsible for binding to an epitope of antigen. The CDR of the heavy and light chains are commonly referred to as CDR1, CDR2 and CDR3, numbered sequentially from the N-terminus.

Various schemes are known in the art for determining the CDR sequence of a given VH or VL amino acid sequence: Kabat complementarity determining regions (CDR) are determined based on sequence variability and are most commonly used (Kabat et al. Sequences of Proteins of Immunological Interest, 5th ed. Public Health Service, National Institutes of Health, Bethesda, Md. (1991)), while Chothia refers to the position of the structural loop (Chothia et al. (1987) J. Mol. Biol. 196: 901-917; Chothia et al. (1989) Nature 342: 877-883), AbM CDR is a compromise between Kabat CDR and Chothia structural loops, and is used by Oxford Molecular's AbM antibody modeling software, "Contact" CDR is based on analysis of available complex crystal structures. The residues of each of these CDRs are described below according to different CDR determination schemes.

| CDR | Kabat Protocol | AbM Protocol | Chothia Protocol | Contact Protocol |
|---|---|---|---|---|
| CDR1 | L24-L34 | L24-L34 | L26-L32 | L30-L36 |
| CDR2 | L50-L56 | L50-L56 | L50-L52 | L46-L55 |
| CDR3 | L89-L97 | L89-L97 | L91-L96 | L89-L96 |
| CDR1 | H31-H35B | H26-H35B | H26-H32 | H30-H35B |
| | | (Kabat numbering system) | | |
| CDR1 | H31-H35 | H26-H35 | H26-H32 | H30-H35 |
| | | (Chothia numbering system) | | |
| CDR2 | H50-H65 | H50-H58 | H53-H55 | H47-H58 |
| CDR3 | H95-H102 | H95-H102 | H96-H101 | H93-H101 |
| | | (Kabat numbering system) | | |

The term "variant" in relation to an antibody refers herein to an antibody comprising a region of the antibody of interest (e.g. a heavy chain variable region or a light chain variable region or a heavy chain CDR region or a light chain CDR region) that has been altered by at least one, e.g. 1-30, or 1-20 or 1-10, e.g. 1 or 2 or 3 or 4 or 5 amino acid substitutions, deletions and/or insertions, wherein the variant substantially retains the biological properties of the antibody molecule before the alteration. In one aspect, the present invention encompasses variants of any of the antibodies described herein. In an embodiment, the antibody variant retains at least 60%, 70%, 80%, 90%, or 100% of the biological activity (e.g. antigen binding capacity) of the antibody before the alteration. It is understood that the heavy chain variable region or the light chain variable region, or each CDR region of an antibody can be altered individually or in combination. In some embodiments, there are no more than 1, 2, 3, 4, 5, 6, 7, 8, 9, or 10 amino acid alterations in one or more or all three heavy chain CDR. Preferably, the amino acid alteration is an amino acid substitution, preferably a conservative substitution.

The term "conservative substitution" refers to the substitution of one amino acid for another amino acid of the same class, e.g. the substitution of one acidic amino acid for another acidic amino acid, the substitution of one basic amino acid for another basic amino acid, or the substitution of one neutral amino acid for another neutral amino acid. Exemplary substitutions are shown in the following table:

| Original Residue | Exemplary Substitution | Preferred Conservative Substitution |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

In some embodiments, the antibody variant has at least 80%, 90% or 95%, or 99% or more amino acid identity to the parent antibody over a region of the antibody sequence of interest.

An "isolated" antibody is an antibody that has been separated from components of its natural environment. In some embodiments, the antibody is purified to greater than 95% or 99% purity, such as, by e.g. electrophoresis (e.g. SDS-PAGE, IEF, capillary electrophoresis) or chromatography (e.g. ion exchange or reverse phase HPLC). For a review of methods for assessing antibody purity, see, e.g. Flatman et al. J. Chromatogr. B848: 79-87 (2007).

An "isolated" nucleic acid refers to a nucleic acid molecule that has been separated from components of its natural environment. An isolated nucleic acid includes a nucleic acid molecule contained in a cell that normally contains the nucleic acid molecule, but the nucleic acid molecule is present extrachromosomally or at a chromosomal location different from its natural chromosomal location.

The term "vector" as used herein refers to a nucleic acid molecule capable of propagating another nucleic acid to which it is associated. The term includes vectors which are self-replicating nucleic acid constructs as well as vectors that are incorporated into the genome of a host cell into which they have been introduced. Some vectors are capable of directing the expression of a nucleic acid to which they are operably linked. Such vectors are referred to herein as "expression vectors".

The terms "host cell", "host cell line", and "host cell culture" are used interchangeably and refer to a cell into which exogenous nucleic acid has been introduced, including the progeny of such cells. Host cells include "transformants" and "transformed cells", which include both primary transformed cells and progeny derived therefrom, regardless of the number of passages. The progeny may not be identical in nucleic acid content to the parent cell but may contain mutations. Included herein are mutant progeny having the same function or biological activity as screened or selected in the originally transformed cell.

Suitable host cells for cloning or expressing vectors encoding antibodies include prokaryotic or eukaryotic cells as described herein. For example, antibodies can be produced in bacteria, particularly when glycosylation and Fc effector function are not desired. For expression of antibody fragments and polypeptides in bacteria, see, e.g. U.S. Pat. Nos. 5,648,237; 5,789,199; and 5,840,523, see also Charlton, Methods in Molecular Biology, vol. 248 (B. K. C. Lo, ed. Humana Press, Totowa, N.J., 2003), pp. 245-254, which describes the expression of antibody fragments in *E. coli*. After expression, the antibody can be isolated from the bacterial cell paste in the soluble fraction and can be further purified.

In an embodiment, the host cell is a eukaryotic cell. In another embodiment, the host cell is selected from yeast cells, mammalian cells, or other cells suitable for the production of antibodies or antigen-binding fragments thereof. For example, eukaryotic microorganisms such as filamentous fungi or yeast are suitable cloning or expression hosts for antibody-encoding vectors, including fungal and yeast strains whose glycosylation pathways have been "humanized", resulting in the production of an antibody with a partially or fully human glycosylation pattern. See Gerngross, Nat. Biotech. 22: 1409-1414(2004), and Li et al. Nat. Biotech. 24: 210-215(2006). Host cells suitable for the expression of glycosylated antibody are also derived from multicellular organisms (invertebrates and vertebrates). Vertebrate cells may also be used as hosts. For example, mammalian cell lines engineered to be suitable for growth in suspension may be used. Other examples of useful mammalian host cell lines are the monkey kidney CV1 line transformed with SV40 (COS-7); human embryonic kidney line (293 or 293 cells, as described, for example, in Graham et al. J. Gen Virol. 36: 59 (1977)) and the like. Other useful mammalian host cell lines include Chinese hamster ovary (CHO) cells, including DHFR-CHO cells (Urlaub et al. Proc. Natl. Acad. Sci. USA 77: 216(1980)); and myeloma cell lines such as YO, NSO and Sp2/0. For a review of certain mammalian host cell lines suitable for antibody production, see, e.g. Yazaki and Wu, Methods in Molecular Biology, vol. 248 (B. K. C. Lo, ed. Humana Press, Totowa, N.J.), pp. 255-268 (2003).

"Percent (%) amino acid sequence identity" relative to a reference polypeptide sequence is defined as the percentage of amino acid residues in a candidate sequence that are identical to the amino acid residues in the reference polypeptide sequence after aligning the sequences (and introducing gaps, if necessary) to obtain the maximum percent sequence identity, without considering any conservative substitutions as part of the sequence identity. Sequence alignments can be performed to determine percent amino acid sequence identity using various methods in the art, for example, using publicly available computer software such as BLAST, BLAST-2, ALIGN, or MEGALIGN (DNASTAR) software. Those skilled in the art can determine appropriate parameters for measuring alignment, including any algorithms needed to obtain maximal alignment over the full length of the sequences being compared.

When percentages of sequence identity are referred to in this application, these percentages are calculated relative to the full length of the longer sequence, unless otherwise specified. Full-length calculations relative to longer sequences apply to both nucleic acid sequences and polypeptide sequences.

"Affinity" or "binding affinity" refers to the intrinsic binding affinity that reflects the interaction between members of a binding pair (e.g. an antibody and an antigen). The affinity of molecule X for its partner Y can generally be expressed in terms of the equilibrium dissociation constant ($K_D$). The equilibrium dissociation constant is the ratio of the dissociation rate constant and the association rate constant ($k_{dis}$ and $k_{on}$, respectively). Affinity can be measured by conventional methods known in the art, including those known in the art and described herein.

In an embodiment of the present invention, an anti-NGF antibody of the present invention has an equilibrium dissociation constant (KD) with NGF of $1\times10^{-7}$ M or less, $1\times10^{-8}$ M or less, $1\times10^{-9}$ M or less, $1\times10^{-10}$ M or less, $1\times10^{-11}$ M or less, $1\times10^{-12}$ M or less, $1\times10^{-13}$ M or less, etc.

An "immunoconjugate" refers to an antibody conjugated to one or more heterologous molecules, including but not limited to carriers.

The term "pharmaceutical composition" refers to a formulation that is present in a form that permits effective biological activity of the active ingredients contained therein, and that does not contain additional ingredients that have unacceptable toxicity to the subject to whom the formulation is administered.

In another aspect, the present invention provides pharmaceutical compositions comprising one or more monoclonal antibodies that bind to NGF or an immunologically active fragment thereof. It will be appreciated that the anti-NGF antibodies or pharmaceutical compositions provided herein can be incorporated into suitable carriers, excipients, and other agents in the formulation for co-administration to provide improved transfer, delivery, tolerance, etc.

The term "pharmaceutically acceptable carrier" refers to a diluent, adjuvant (e.g. Freund's adjuvant (complete and incomplete)), excipient, or vehicle co-administered with a therapeutic agent.

Pharmaceutical carriers suitable for use in the present invention may be conventional, see pharmaceutical formulation adjuvants described in "Handbook of Pharmaceutical Excipients", 7th Edition, R. C. Rowe, P. J. Seskey and S. C. Owen, Pharmaceutical Press, London, Chicago; and compositions and formulations suitable for drug delivery of the disclosed antibodies described in "Remington'S pharmaceutical Sciences", E. W. Martin, Mack Publishing Co, Easton, Pa. Press, 21st Edition, 2012, which describes.

The term "effective amount" refers to an amount or dose sufficient to achieve, or at least partially achieve, the desired effect after administration in single or multiple doses; "therapeutically effective amount" refers to an amount that produces the desired effect in the treated subject, including an improvement in the subject's condition (e.g. an improvement in one or more symptoms) and/or a delay in the progression of symptoms, etc. An effective amount to prevent a disease refers to an amount sufficient to prevent, stop or delay the onset of the disease. Determination of an effective amount is well within the capability of those skilled in the art, e.g. a therapeutically effective amount depends on the particular disease involved; the extent or severity of the disease; individual patient's response; the specific antibody administered; mode of administration; the bioavailability profile of the administered formulation; the selected dosing regimen; and the use of any concomitant therapy, etc.

As used herein, "treating" refers to slowing, interrupting, arresting, relieving, stopping, reducing, or reversing the progression or severity of an existing symptom, disorder, condition, or disease.

The term "subject" or "individual" is a primate (e.g. a human and a non-human primate such as a monkey). In certain embodiments, the individual or subject is a human.

"Alleviating" pain or one or more symptoms of pain means reducing or improving one or more symptoms of pain as compared to not administering the anti-NGF antibody. "Remission" also includes shortening or reducing the duration of a symptom.

The term "pain" refers to any etiology, including acute and chronic pain as well as any pain with an inflammatory component. As used herein, "pain" includes nociception and perception of pain, and pain can be assessed objectively and subjectively using pain scores and other methods known in the art.

The term "hyperalgesia" refers to an increased pain response of the body to a normally noxious or unpleasant stimulus.

1.2 Sequence of an Exemplary Anti-NGF Antibody TRN1027 of the Present Invention

TABLE I

| Heavy and light chain variable region sequences of antibody TRN1027: | | |
|---|---|---|
| VH | SEQ ID NO: 7 | QLQLQESGSGLVRPSQTLSLTCAVSGDSMNSGGYSWSWIRQ<br>PPGKGLEWIGYIYYSGSTHYNPSLESRVTLSLHRSKNQFFLQ<br>LSSVTAADTAVYYCARTLWFGEFEGFDPWGQGILVTVSS |
| VL | SEQ ID NO: 8 | QSALTQPPSASGSPGQSVTISCTGTSSDVGGYNFVSWYQHH<br>PGKAPKLLLYEVSKRPSGVPDRFSGSKSGNTASLTVSGLQAE<br>DEADYFCSSFAGSNNFVFFGGGTKLTVL |

SEQ ID NO: 9
ASTKGPSVFPLAPCSRSTSESTAALGCLVKDYFPEPVTVSWNSGALTSGVHTFPAVLQSSGLYSLSSVVTVPS
SSLGTKTYTCNVDHKPSNTKVDKRVESKYGPPCPPCPAPEFLGGPSVFLFPPKPKDTLMISRTPEVTCVVVD
VSQEDPEVQFNWYVDGVEVHNAKTKPREEQFNSTYRVVSVLTVLHQDWLNGKEYKCKVSNKGLPSSIEK
TISKAKGQPREPQVYTLPPSQEEMTKNQVSLTCLVKGFYPSDIAVEWESNGQPENNYKTTPPVLDSDGSFFL
YSRLTVDKSRWQEGNVFSCSVMHEALHNHYTQKSLSLSLGK

SEQ ID NO: 10
GQPKAAPSVTLFPPSSEELQANKATLVCLISDFYPGAVTVAWKADSSPVKAGVETTTPSKQSNNKYAASSYL
SLTPEQWKSHRSYSCQVTHEGSTVEKTVAPTECS

TABLE II

CDR sequence of antibody TRN1027:

| | CDR | SEQ ID NO: | Sequence |
|---|---|---|---|
| VH | CDR1 | 1 | **GDSMNSGGYS** |
| | CDR2 | 2 | **IYYS** |
| | CDR3 | 3 | **ARTLWFGEFEGFDP** |
| VL | CDR1 | 4 | **SSDVGGYNF** |
| | CDR2 | 5 | **EVS** |
| | CDR3 | 6 | **SSFAGSNNFVF** |

EXAMPLES

The following examples further illustrate the present invention, however, it should be understood that the examples have been described by way of illustration and not limitation and that various modifications may be made by those skilled in the art.

The practice of the present invention will employ, unless expressly stated to the contrary, conventional methods of chemistry, biochemistry, organic chemistry, molecular biology, microbiology, recombinant DNA techniques, genetics, immunology, and cell biology within the skill of the art. These methods are described, for example, in Sambrook et al. Molecular Cloning: A Laboratory Manual (3rd ed. 2001); Sambrook et al. Molecular Cloning: A Laboratory Manual (2nd ed. 1989); Maniatis et al. Molecular Cloning: A Laboratory Manual (1982); Ausubel et al. Current Protocols in Molecular Biology (John Wiley and Sons, updated in July 2008); Short Protocols in Molecular Biology: A Compendium of Methods from Current Protocols in Molecular Biology, Greene Pub. Associates and Wiley-Interscience; Glover, DNA Cloning: A Practical Approach, vol. I&II (IRL Press, Oxford, 1985); Anand, Techniques for the Analysis of Complex Genomes, (Academic Press, New York, 1992); Transcription and Translation (B. Hames & S. Higgins, Eds., 1984); Perbal, A Practical Guide to Molecular Cloning (1984); Harlow and Lane, Antibodies, (Cold Spring Harbor Laboratory Press, Cold Spring Harbor, N.Y., 1998) Current Protocols in Immunology Q. E. Coligan, A. M. Kruisbeek, D. H. Margulies, E. M. Shevach and W. Strober, eds., 1991); Annual Review of Immunology; and journal monographs such as Advances in Immunology.

The following examples are put forth so as to provide those of ordinary skill in the art with a complete disclosure and description of how to make and use the methods and compositions of the present invention and are not intended to limit the scope of what is claimed.

Example 1. Preparation of Human Anti-NGF Antibodies

1) PBMC Separation

Patients with various diseases were injected with murine nerve growth factor (JINLUJIE), and co-treated for 30 days (according to the doctor's advice), 10 mL peripheral blood was collected into heparin-containing anticoagulant tube, and plasma and PBMC cells were separated by density centrifugation. The specific operations were as follows: 10 mL venous blood was taken and centrifuged at 400 g, 22° C. for 15 min; the supernatant transparent plasma layer after centrifugation was aspirated and dispensed at −80° C. for cryopreservation; the remaining part was mixed with an equal amount of RPMI1640 culture medium; the mixture was slowly added into a sterile centrifuge tube containing lymphocyte separation solution Ficoll, and the liquid level layer was kept intact; 2000 rpm horizontal centrifugation was performed for 20 min; the PBMC cells located in the misty layer was sucked up using a capillary, placed into another sterile centrifuge tube, and added with 5 times volume of RPMI1640 culture medium; 1500 rpm centrifugation was performed for 10 min; after repeating the wash twice, the cells were counted, and cryo-preserved at −80° C. at $1\times10^7$ cells/tube for later use.

2) Anti-NGF Antibody Titer Detection

HNGF (Sino Biological) was diluted to 2 mg/mL with the phosphate coating buffer of pH 9.6, added to a 96-well plate at 0.1 mL/well, coated overnight at 4° C., and blocked with a blocking buffer for 2 h at 37° C. 100 μL of serially diluted plasma samples were added as a primary antibody and incubated for 1 h at 37° C. Then a secondary antibody labeled with HRP goat anti-human IgG (diluted at 1:10000) was added and incubated for 1 h at 37° C. Then 100 μL/well of substrate developing solution TMB was added. After being placed in the dark at 37° C. for 5 min, the reaction was stopped with 2M sulfuric acid, and the OD450 value was read. The results showed that sample Ns006 had a higher absorbance (FIG. 1), indicating that the anti-NGF antibody titer in the serum sample of Ns006 was higher and could bind to hNGF. The PBMC labeled as Ns006 sample was then flow-sorted.

3) Single Plasma Cell Sorting by Flow Cytometry

According to the above serological test results, single plasma cells were sorted from PBMC of Ns006 sample by flow cytometry (BD, Facs Aria Sorp). Gated CD3/CD14/CD16/cd235a− CD19+CD20+/− CD38hi CD27hi was set to sort specific cell populations from PBMC. Cell populations (>3%) of memory plasma cells specific to the hNGF protein were sorted. Individual plasma cells were plated in 96-well PCR plates (20 µL of single-cell lysate per well) so that each well contained one plasma cell and preserved in a −80° C. freezer for later use.

4) Isolation of Antibody Variable Region Genes from Individual Plasma Cells

First, the first strand of cDNA was synthesized by reverse transcription from the memory plasma cells obtained in step 3) of Example 1 using a constant region primer (see the primer information disclosed in CN107760690B) and Superscript III reverse transcriptase (Invitrogen, Carlsbad, Calif.). The antibody genes were then isolated by the PCR procedure described below.

First round PCR: 50 µL system, adding 5 µL of the reverse transcription reaction product, 25 µL of Taq enzyme Mix, 25 µM of each subtype heavy and light chain antibody constant region primers. Reaction conditions:

Pre-denaturation at 95° C. for 5 min;

Cycle Conditions: denaturation at 94° C. for 30 s, annealing at 55° C. for 60 s, and extension at 72° C. for 90 s; repeating the cycles for 35 times;

Finally, the extension was performed at 72° C. for 7 min. The reaction product was used for the second round of PCR reaction.

Second round PCR: 50 µL system, adding 3 µL of the first round PCR reaction product, 25 µL of Taq enzyme Mix, 20 µM of each subtype heavy and light chain antibody variable region primers. Reaction conditions:

Pre-denaturation at 95° C. for 5 min;

Cycle Conditions: denaturation at 94° C. for 30 s, annealing at 58° C. for 60 s (or Lambda chain annealing at 64° C. for 60 s), and extension at 72° C. for 90 s; repeating the cycles for 35 times;

Finally, the extension was performed at 72° C. for 7 min. The obtained PCR product was identified by 1.2% agarose gel electrophoresis to obtain a variable region gene. Its heavy chain variable region amino acid sequence VH is shown in SEQ ID NO:7 and its light chain variable region amino acid sequence VL is shown in SEQ ID NO:8.

5) Construction, Expression, and Purification of Recombinant Antibody Expression Vector In an example, the PCR product of the antibody variable region gene identified above was cloned into the pcDNA3.1+/C-(K)-DYK plasmid containing the human IgG constant region using conventional methods to construct an expression vector for human anti-NGF antibody. The expression vector is then transformed into *E. coli* DH5α competent bacteria for vector amplification. The vector (recombinant plasmid) was extracted. The obtained recombinant plasmid was co-transfected into HEK293 cells. Then the HEK293 cells were cultured and the antibody was expressed according to the conventional method. The culture supernatant was collected and centrifuged at 4000 rpm for 1 h. The supernatant was purified by Protein A affinity chromatography. Purified antibodies were tested for expression and purification by SDS-PAGE. The result of SDS-PAGE test showed that the antibody was successfully expressed. The antibody was named TRN1027, its relative molecular weight was about 180 KD, its heavy chain was about 55 KD and its light chain was about 30 KD.

Example 2. Antibody Binding Activity Assay

Figure 2:
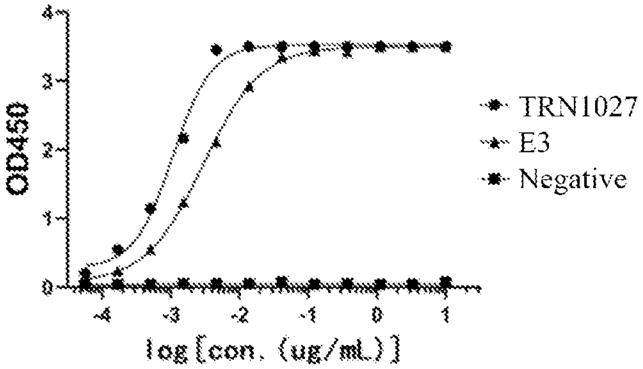
FIG. 2: test results of antibody binding activity.

Antibody TRN1027 was tested for binding activity to hNGF by the ELISA assay. Specifically, 2 µg/mL of hNGF as an antigen was diluted and coated with carbonate buffer at pH 9.6 in a 96-well plate overnight at 4° C.; the plate was blocked by the blocking solution at 37° C. for 2 h. The antibody TRN1027 was serial diluted with the blocking solution, starting at 10 µg/mL, 3-fold dilution for 12 gradients; each gradient of antibody TRN1027 was then added to a 96-well plate and incubated for 1 h at 37° C. The plate was washed with the PBST buffer, added with 100 µ/well LHRP labeled goat anti-human IgG (1:10000), and incubate at 37° C. for 1 h. The plate was washed with the PBST buffer, added with 100 µL/well TMB developing solution away from light, and placed for 5 min at 37° C. $H_2SO_4$ was added to stop the reaction. The detection was conducted at 450 nm wavelength. The results were calculated and analyzed. In this experiment, the anti-NGF antibody Tanezumab (CAS No. 880266-57-9, published in CN 102746399 B, also known as E3) disclosed in the prior art with good effect was used as a positive control. The results showed (see FIG. 2) that: EC50 of E3 binding to hNGF was 2.96 ng/mL; however, the human anti-NGF antibody TRN1027 of the present application binds to hNGF with an EC50 of 1.067 ng/mL, indicating that the human anti-NGF antibody TRN1027 has a strong binding activity.

Example 3. Binding Affinity of the Antibody

The binding force between an antibody and an antigenic determinant, called antibody affinity, reflects the ability of the antibody molecule to bind to the antigenic determinant. In this example, the antigen binding affinity of antibody TRN1027 was detected using surface plasmon resonance analysis (BIACORE3000). Anti-human IgG (Fc) antibody was immobilized on the surface of CM5 sensor chip (GE) by amino-coupling method. The anti-NGF antibody was captured as a ligand, the capture level reached about 400 RU. Different concentrations of hNGF protein were passed through the detection channel as the analyte streams. The binding of antigen to antibody and dissociation of the bound complex was monitored in real-time. Kinetic analysis (calculation of dissociation constants (KD)) was performed with the Biacore X100 Evaluation Software (2.0.1).

Figure 3:
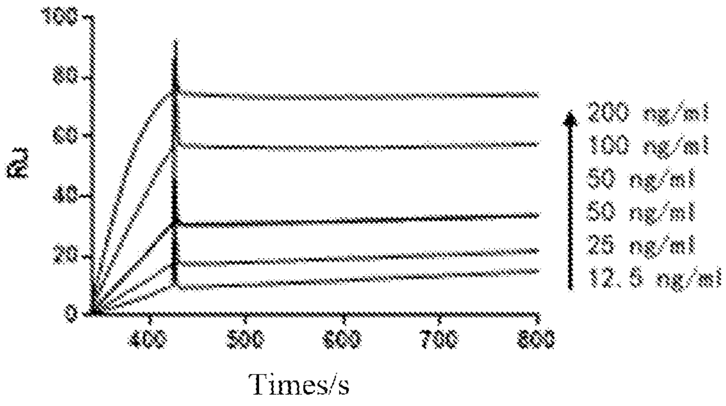
FIG. 3: antibody TRN1027 affinity curve.

The results in FIG. 3 showed that the dissociation constant of TRN1027 was as low as 1.68E-11 M, indicating that the antibody TRN1027 has a strong binding affinity to the antigen hNGF.

Example 4. Neutralizing Activity of the Antibody

In this example, TF-1 cells (human erythroid leukemia cells) were used to test the ability of anti-NGF antibodies to block NGF-dependent TrkA receptor-mediated cell proliferation activity (Chevalier et al. Blood (1994), 83 (6): 1479-1485). NGF is capable of binding to TrkA. As a high-affinity receptor for NGF, TrkA forms a dimer after binding to NGF, which activates the intracellular domain tyrosine kinase domain, and causes corresponding tyrosine phosphorylation, thereby activating the downstream signal transduction system and performing the function of regulating the target cells, thereby inducing the proliferation of TF-1 cells.

The TF-1 cells (ATCC, CRL-2003™) in the logarithmic phase were placed at 37° C. and starved for 24 h in 5% $CO_2$. An NGF solution with a concentration of 32 ng/mL was prepared with the minimal medium and added to a 96-well plate in the quantity of 25 uL per well. A solution of the antibody of the present invention at a concentration of 6 ug/mL was prepared with the minimal medium as a starting concentration, followed by a 3-fold dilution to obtain 8 concentration gradients. Each well of the 96-well plate was added with 25 uL of serial dilution of human anti-NGF antibody and incubated for 30 min at 37° C. Each well of the 96-well plate was added with 50 uL of TF-1 cells at a density of $6\times10^5$/mL starved for 24 h. The final hNGF concentration was 8 ng/mL and the final cell density was $3\times10^5$/mL. After incubation for 72 h, the plate was added with MTS reagent, and incubated at 37° C. for 2 h. The detection was performed. The signal dependence on antibody concentration was analyzed by calculating the EC50 of antibody TRN1027 by the absorbance, with the E3 antibody as a control.

Figure 4:
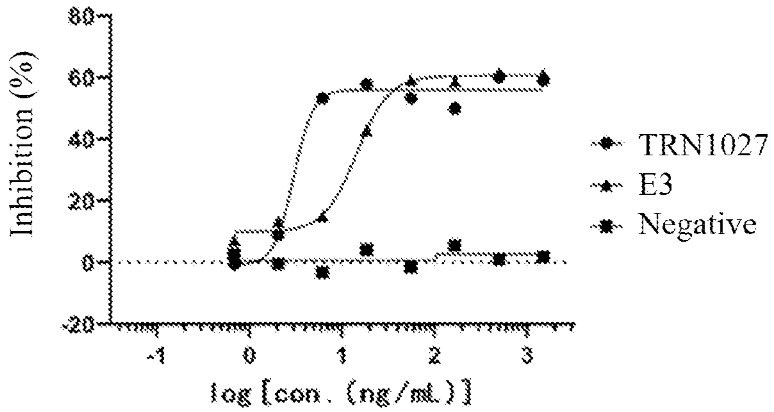
FIG. 4: antibody TRN1027 inhibits TF-1 cell proliferation.

The results (FIG. 4) showed that the dose-response curves for antibody TRN1027 and the control E3 antibody are typical S-shaped dose-response curves. Calculations showed that the EC50 of the antibody TRN1027 and the control are 3.01 ng/mL and 14.35 ng/mL, respectively. The antibodies of the present invention were shown to inhibit NGF-induced proliferation of TF-1 cells with better neutralizing activity.

In addition, this example also examined the neutralizing activity of the antibody TRN1027 using PC-12 cells. The PC-12 cell line is derived from a transplantable murine pheochromocytoma and has a reversible neuronal phenotypic response to NGF. This cell line highly expresses NGF receptor TrkA. PC-12 cells are induced by physiological levels of NGF to differentiate into cells with sympathetic neuron characteristics, which are often used to analyze growth factor-related mechanisms and neuronal differentiation studies.

First, a 32 ng/mL NGF solution was prepared with the basic medium of PC-12 cells, and 25 uL per well was added to a 96-well flat-bottom cell culture plate. A solution of the antibody of the present invention at a concentration of 6 ug/mL was prepared with the minimal medium as a starting concentration, followed by a 3-fold dilution to obtain 8 concentration gradients. The 96-well plate was added with 25 uL of serial dilution of human anti-NGF antibody of the present invention each well and incubated for 30 min at 37° C. Then 50 uL of PC-12 cells at a density of $2\times10^5$/mL were added to each well of the 96-well plate and cultured for an additional 48 h. Celltiter-Glo chemiluminescent cell viability assay kit was used to detect and calculate the results.

NGF promotes differentiation and synapse formation of PC-12 cells by binding to TrkA, and enhances metabolic activity in PC-12 cells. The light signal is proportional to the amount of ATP in the system, and ATP is positively correlated with the number of living cells. Thus, the amount of ATP can be measured to determine the activity of the cells. The calculated results showed that the dose-response curves of TRN1027 and E3 are typical S-shaped dose-response curves with EC50 of 8.826 ng/mL and 32.21 ng/mL, respectively. It is shown that the antibody of the present invention has higher neutralizing activity, and can neutralize NGF and block its binding receptor TrkA, thereby inhibiting the differentiation of PC-12 cells induced by NGF.

Example 5. Cross-Reaction of Antibodies with BDNF, NT-3, and NT-4

The present invention determines the cross-reactivity of antibody TRN1027 to other neurotrophins by ELISA. HBDNF, hNT-3 and hNT-4 (Absin) were used as antigens to coat the 96-well plate at 200 ug/well overnight at 4° C., respectively. Then the plate was blocked with the blocking solution for 2 hours at ambient temperature. The plate was added with antibody TRN1027 with decreasing concentrations (ranging from 10 ug/ml-0 ug/ml) at 100 ul/well and incubated at 37° C. for 1 h. Antibody TRN1027 was detected by TMB with goat-anti-human IgG-HRP (1:10000) and the substrate developer. OD values were measured at dual wavelengths of 450-630 nm.

The results showed that the antibody TRN1027 at each concentration did not bind to hBDNF, hNT-3, and hNT-4, so it was clear that the NGF antibody does not cross-react with BDNF, NT-3, and NT-4. NT-3, NT-4, and BDNF all belong to the neurotrophic family, and they have high homology with NGF in amino acid sequence, spatial structure, and biological function. The inventors believe that the anti-NGF antibody of the present invention only specifically binds to NGF without interfering with the biological activity of other neurotrophic factors. This feature can show a more direct therapeutic effect in the clinical application of the antibody.

Example 6. Anti-Hyperalgesic Activity of an Antibody

To assess the role of the antibody TRN1027 in modulating pain, the following experiments were performed. Mice (C57BL/6N, male) were selected and the Mechanical Withdrawal Threshold (MWT) of the plantar aspect of the left hind paw was determined 3 times using VonFrey (IITC) fibers, and the mean value of 3 times was taken as the base pain threshold. The next day (Day 1), except the blank control group, the remaining groups of mice were injected intraplantar with 30 μl of CFA (3 mg/ml) in plantar aspect of the left hind paw to induce inflammation. After 24 h (Day 2), the left hind paw MWT of the mice was detected 3 times in the same method, and the mean value was taken as the pain threshold before administration. Animals with too large or too small MWT were excluded. 45 animals were chosen and divided into 5 groups (n=9) according to the average MWT value. The animals were then injected with PBS or test substances subcutaneously: the first group was the blank control group, administrated with PBS; the second group was the model control group, administrated with PBS; the third, fourth, and fifth groups were administrated with TRN1027, E3, and the negative control antibody at 10 mg/kg, respectively. The pain threshold was measured at 24 h (Day 3), 48 h (Day 4), and 72 h (Day 5) after administration, and the pain threshold increase rate after administration was calculated.

Percent pain threshold increase rate=(MWT administration group-MWT model group)/MWT model group×100%.

Figure 5:
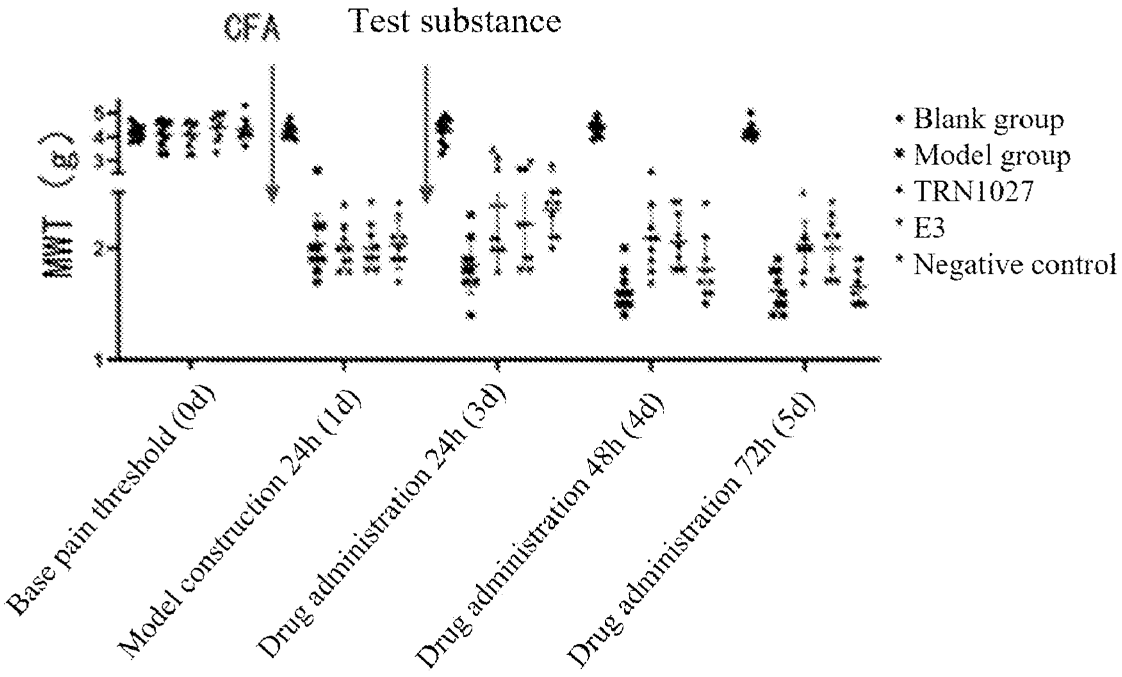
FIG. 5: effect of a single subcutaneous dose on CFA-induced inflammatory pain MWT in mice (n=9).

There were no significant differences in MWT values between mice of TRN1027, E3, and negative control groups 24 h after a single subcutaneous injection. The MWT values in the TRN1027 group and E3 group were significantly higher than those in the model group (P<0.01-0.001), and the pain threshold increase rates were 28.77% and 26.03%, respectively. At 72 h after administration, MWT in TRN1027 and E3 groups still had a statistically significant difference compared with the model group (P<0.01-0.001), and the pain threshold increase rate was higher than 20%. The MWT value of the negative control antibody group was slightly higher than that of the model group, but the difference had no statistical significance (P>0.05) (FIG. 5, table 1). Therefore, it showed that the antibody TRN1027 has a significant pain alleviating and treating effect on the inflammatory response induced by CFA, namely, the human anti-NGF antibody of the present invention has anti-hyperalgesia activity.

TABLE 1

Pain thresholds for CFA-induced inflammatory responses following a single subcutaneous injection dose

| | Pain threshold increase rate after administration (%) | | |
|---|---|---|---|
| Group (10 mg/kg) | 24 h (Day 3) | 48 h (Day 4) | 72 h (Day 5) |
| TRN1027 | 28.92 | 28.77 | 24.66 |
| E3 | 19.88 | 26.71 | 23.29 |
| Negative control antibody | 27.11 | 11.64 | 2.05 |

What is claimed is:

1. A human antibody or antigen-binding fragment thereof that specifically binds to human nerve growth factor (NGF), comprising:

(a) a heavy chain variable region comprising the following CDRs:

CDR1 comprising the sequence of SEQ ID NO: 1;

CDR2 comprising the sequence of SEQ ID NO: 2;

CDR3 comprising the sequence of SEQ ID NO: 3, and (b) a light chain variable region comprising the following CDRs:

CDR1 comprising the sequence of SEQ ID NO: 4;

CDR2 comprising the sequence of SEQ ID NO: 5;

CDR3 comprising the sequence of SEQ ID NO: 6.

2. The human antibody or antigen-binding fragment thereof according to claim 1, wherein the heavy chain variable region is selected from:

(1) a sequence comprising the heavy chain CDRs of claim 1 and having at least 80% identity to SEQ ID NO: 7; and (2) a sequence comprising SEQ ID NO: 7.

3. The antibody or antigen-binding fragment thereof according to claim 1, wherein the light chain variable region is selected from:

(1) a sequence comprising the light chain CDRs of claim 1 and having at least 80% identity to SEQ ID NO: 8;

(2) a sequence comprising SEQ ID NO: 8.

4. The antibody or antigen-binding fragment thereof according to claim 1, wherein the antibody is a human monoclonal antibody.

5. The antibody or antigen-binding fragment thereof according to claim 1, wherein the antigen-binding fragment is selected from a Fab, Fab'-SH, scFv, or (Fab')2 fragment.

6. The antibody or antigen-binding fragment thereof according to claim 1, comprising a constant region sequence, wherein the constant region sequence is a human consensus constant region sequence.

7. The antibody or antigen-binding fragment thereof according to claim 1, wherein a heavy chain constant region of the antibody comprises the amino acid sequence shown in SEQ ID NO:9, and a light chain constant region comprises the amino acid sequence shown in SEQ ID NO:10.

8. A pharmaceutical composition comprising the antibody or antigen-binding fragment thereof according to claim 1 and a pharmaceutically acceptable carrier.

* * * * *

SEQUENCE LISTING

<160> NUMBER OF SEQ ID NOS: 10

<210> SEQ ID NO 1
<211> LENGTH: 10
<212> TYPE: PRT
<213> ORGANISM: Artificial Sequence
<220> FEATURE:
<223> OTHER INFORMATION: HCDR1

<400> SEQUENCE: 1

```
Gly Asp Ser Met Asn Ser Gly Gly Tyr Ser
1               5                   10
```

<210> SEQ ID NO 2
<211> LENGTH: 4
<212> TYPE: PRT
<213> ORGANISM: Artificial Sequence
<220> FEATURE:
<223> OTHER INFORMATION: HCDR2

<400> SEQUENCE: 2

```
Ile Tyr Tyr Ser
1
```

<210> SEQ ID NO 3
<211> LENGTH: 14
<212> TYPE: PRT
<213> ORGANISM: Artificial Sequence
<220> FEATURE:
<223> OTHER INFORMATION: HCDR3

<400> SEQUENCE: 3

```
Ala Arg Thr Leu Trp Phe Gly Glu Phe Glu Gly Phe Asp Pro
1               5                   10
```

<210> SEQ ID NO 4
<211> LENGTH: 9
<212> TYPE: PRT
<213> ORGANISM: Artificial Sequence
<220> FEATURE:
<223> OTHER INFORMATION: LCDR1

<400> SEQUENCE: 4

```
Ser Ser Asp Val Gly Gly Tyr Asn Phe
1               5
```

<210> SEQ ID NO 5

<211> LENGTH: 3
<212> TYPE: PRT
<213> ORGANISM: Artificial Sequence
<220> FEATURE:
<223> OTHER INFORMATION: LCDR2

<400> SEQUENCE: 5

Glu Val Ser
1

<210> SEQ ID NO 6
<211> LENGTH: 11
<212> TYPE: PRT
<213> ORGANISM: Artificial Sequence
<220> FEATURE:
<223> OTHER INFORMATION: LCDR3

<400> SEQUENCE: 6

```
Ser Ser Phe Ala Gly Ser Asn Asn Phe Val Phe
1               5                   10
```

<210> SEQ ID NO 7
<211> LENGTH: 122
<212> TYPE: PRT
<213> ORGANISM: Artificial Sequence
<220> FEATURE:
<223> OTHER INFORMATION: VH

<400> SEQUENCE: 7

```
Gln Leu Gln Leu Gln Glu Ser Gly Ser Gly Leu Val Arg Pro Ser Gln
1               5                   10                  15

Thr Leu Ser Leu Thr Cys Ala Val Ser Gly Asp Ser Met Asn Ser Gly
            20                  25                  30

Gly Tyr Ser Trp Ser Trp Ile Arg Gln Pro Pro Gly Lys Gly Leu Glu
        35                  40                  45

Trp Ile Gly Tyr Ile Tyr Tyr Ser Gly Ser Thr His Tyr Asn Pro Ser
    50                  55                  60

Leu Glu Ser Arg Val Thr Leu Ser Leu His Arg Ser Lys Asn Gln Phe
65                  70                  75                  80

Phe Leu Gln Leu Ser Ser Val Thr Ala Ala Asp Thr Ala Val Tyr Tyr
                85                  90                  95

Cys Ala Arg Thr Leu Trp Phe Gly Glu Phe Glu Gly Phe Asp Pro Trp
            100                 105                 110

Gly Gln Gly Ile Leu Val Thr Val Ser Ser
        115                 120
```

<210> SEQ ID NO 8
<211> LENGTH: 111
<212> TYPE: PRT
<213> ORGANISM: Artificial Sequence
<220> FEATURE:
<223> OTHER INFORMATION: VL

<400> SEQUENCE: 8

```
Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Phe Val Ser Trp Tyr Gln His His Pro Gly Lys Ala Pro Lys Leu
        35                  40                  45

Leu Leu Tyr Glu Val Ser Lys Arg Pro Ser Gly Val Pro Asp Arg Phe
    50                  55                  60
```

Ser Gly Ser Lys Ser Gly Asn Thr Ala Ser Leu Thr Val Ser Gly Leu
65 70 75 80

Gln Ala Glu Asp Glu Ala Asp Tyr Phe Cys Ser Ser Phe Ala Gly Ser
85 90 95

Asn Asn Phe Val Phe Phe Gly Gly Gly Thr Lys Leu Thr Val Leu
100 105 110

<210> SEQ ID NO 9
<211> LENGTH: 327
<212> TYPE: PRT
<213> ORGANISM: Artificial Sequence
<220> FEATURE:
<223> OTHER INFORMATION: Heavy chain constant region

<400> SEQUENCE: 9

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Lys Thr
65 70 75 80

Tyr Thr Cys Asn Val Asp His Lys Pro Ser Asn Thr Lys Val Asp Lys
85 90 95

Arg Val Glu Ser Lys Tyr Gly Pro Pro Cys Pro Pro Cys Pro Ala Pro
100 105 110

Glu Phe Leu Gly Gly Pro Ser Val Phe Leu Phe Pro Pro Lys Pro Lys
115 120 125

Asp Thr Leu Met Ile Ser Arg Thr Pro Glu Val Thr Cys Val Val Val
130 135 140

Asp Val Ser Gln Glu Asp Pro Glu Val Gln Phe Asn Trp Tyr Val Asp
145 150 155 160

Gly Val Glu Val His Asn Ala Lys Thr Lys Pro Arg Glu Glu Gln Phe
165 170 175

Asn Ser Thr Tyr Arg Val Val Ser Val Leu Thr Val Leu His Gln Asp
180 185 190

Trp Leu Asn Gly Lys Glu Tyr Lys Cys Lys Val Ser Asn Lys Gly Leu
195 200 205

Pro Ser Ser Ile Glu Lys Thr Ile Ser Lys Ala Lys Gly Gln Pro Arg
210 215 220

Glu Pro Gln Val Tyr Thr Leu Pro Pro Ser Gln Glu Glu Met Thr Lys
225 230 235 240

Asn Gln Val Ser Leu Thr Cys Leu Val Lys Gly Phe Tyr Pro Ser Asp
245 250 255

Ile Ala Val Glu Trp Glu Ser Asn Gly Gln Pro Glu Asn Asn Tyr Lys
260 265 270

Thr Thr Pro Pro Val Leu Asp Ser Asp Gly Ser Phe Phe Leu Tyr Ser
275 280 285

Arg Leu Thr Val Asp Lys Ser Arg Trp Gln Glu Gly Asn Val Phe Ser
290 295 300

Cys Ser Val Met His Glu Ala Leu His Asn His Tyr Thr Gln Lys Ser
305 310 315 320

-continued

```
Leu Ser Leu Ser Leu Gly Lys
                325


<210> SEQ ID NO 10
<211> LENGTH: 106
<212> TYPE: PRT
<213> ORGANISM: Artificial Sequence
<220> FEATURE:
<223> OTHER INFORMATION: Light chain constant region

<400> SEQUENCE: 10

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```